US007947042B2

(12) United States Patent  (10) Patent No.: US 7,947,042 B2
Osman  (45) Date of Patent: May 24, 2011

(54) BIOLOGIC INTRAMEDULLARY FIXATION DEVICE AND METHODS OF USE

(76) Inventor: Said G Osman, Russellville, AL (US)

( * ) Notice: Subject to any disclaimer, the term of this patent is extended or adjusted under 35 U.S.C. 154(b) by 175 days.

(21) Appl. No.: 11/861,509

(22) Filed: Sep. 26, 2007

(65) Prior Publication Data

US 2008/0077140 A1  Mar. 27, 2008

Related U.S. Application Data

(60) Provisional application No. 60/847,360, filed on Sep. 27, 2006.

(51) Int. Cl.
*A61B 17/58* (2006.01)
(52) U.S. Cl. ............................................. 606/62; 606/92
(58) Field of Classification Search .................... 606/60, 606/62–68, 88, 279, 300, 304, 92–95, 323; 623/20.14–20.31, 20.35–20.36, 22.4
See application file for complete search history.

(56) References Cited

U.S. PATENT DOCUMENTS

| | | | |
|---|---|---|---|
| 4,065,817 A * | 1/1978 | Branemark et al. | 623/23.46 |
| 4,653,487 A | 3/1987 | Maale | |
| 4,961,740 A * | 10/1990 | Ray et al. | 606/247 |
| 5,211,664 A * | 5/1993 | Tepic et al. | 623/16.11 |
| 5,514,137 A * | 5/1996 | Coutts | 606/62 |
| 6,387,098 B1 * | 5/2002 | Cole et al. | 606/62 |
| 2004/0015172 A1 * | 1/2004 | Biedermann et al. | 606/73 |
| 2004/0225360 A1 * | 11/2004 | Malone | 623/17.11 |
| 2005/0015154 A1 * | 1/2005 | Lindsey et al. | 623/23.46 |

FOREIGN PATENT DOCUMENTS

| | | |
|---|---|---|
| DE | 39 19 900 | 12/1990 |
| RU | 1503778 | 8/1989 |
| WO | WO 98/49962 | 11/1998 |

* cited by examiner

*Primary Examiner* — Eduardo C Robert
*Assistant Examiner* — Lynnsy Schneider
(74) *Attorney, Agent, or Firm* — Nixon & Vanderhye P.C.

(57) ABSTRACT

A biologic intramedullary fixation device for treating a bone fracture includes an internal tubular wall formed of a bioabsorbable synthetic material; and an outer wall coupled with and surrounding the internal tubular wall with an annular space therebetween. The outer wall is at least partially fenestrated and is formed of the bioabsorbable synthetic material. A biologically replaceable cement material is injectable into the annular space between the internal tubular wall and the outer wall.

1 Claim, 3 Drawing Sheets

US 7,947,042 B2

BIOLOGIC INTRAMEDULLARY FIXATION DEVICE AND METHODS OF USE

CROSS-REFERENCES TO RELATED APPLICATIONS

This application claims the benefit of U.S. Provisional Patent Application Ser. No. 60/847,360, filed Sep. 27, 2006, the entire content of which is herein incorporated by reference.

STATEMENT REGARDING FEDERALLY SPONSORED RESEARCH OR DEVELOPMENT (Not Applicable)

BACKGROUND OF THE INVENTION

Treatment of fractures of the long bones has evolved through many phases over the last half century from external splintage, tractions, plasta casting, open reduction and internal fixation with various types of plates, open intramedullary rods to current methods of intramedullary rods supplemented with interlocking screws for better stabilization, control of rotational deformities and maintenance of normal length of the fractured bone.

The materials used for internal fixation of these fractures have included largely various metal alloys. A limited number of bioabsorbable devices have been used to fix smaller bone fractures, but no serious attempt has been made for larger bones such as the femur, tibia, humerus, radius and ulna. Problems arise, however, in that once the fracture has healed, the metal device remains in place and often requires a second operation to remove it.

BRIEF SUMMARY OF THE INVENTION

A concept of using biologic techniques allows us to achieve satisfactory fracture management while eliminating a number of undesirable consequences of current methods of internal fixation including but not limited to:

1) minimally invasive technique: less trauma associated with the surgical technique reduces surgical complications, reduces surgical pain, reduces convalescence, reduces cosmetic deformity;

2) immediate stable fixation and early rehabilitation of the limb;

3) the biologic cement material, e.g., hydroxyapatite, will be resorbed over time and replaced by the host's bone;

4) the synthetic rod made out of a bioabsorbable (or bioincorporable) material will over time be degraded and removed by the body's macrophage system (or incorporated into the host bone);

5) the biologic system eliminates the need for a second operation for the removal of a fixation device.

The concept can be used for fractures of all long bones, e.g., phalangial bones of hands, metacarpals, radius, ulna, humerus, clavicle, femur, tibia, fibula and metatarsal bones.

In an exemplary embodiment, a biologic intramedullary fixation device for treating a bone fracture includes an internal tubular wall formed of a bioabsorbable synthetic or bioincorporable material; and an outer wall coupled with and surrounding the internal tubular wall with an annular space therebetween. The outer wall is at least partially fenestrated and is formed of the bioabsorbable synthetic or bioincorporable material. A biologically replaceable cement material is injectable into the annular space between the internal tubular wall and the outer wall.

The internal tubular wall may be partially fenestrated adjacent the bone fracture. With the internal tubular wall defining an internal cavity, a top of the internal cavity may be sealed with a set screw. In this context, a bottom of the internal tubular cavity is left open to allow in-growth of vessels and resorption of the device.

The internal tubular wall may be ribbed, and the outer wall is preferably entirely fenestrated except for its proximal and distal ends. In one arrangement, the fenestrations in the outer wall are more prominent adjacent the bone fracture.

The device may additionally include inter-wall connectors connecting the internal tubular wall and the outer wall. In this context, the inter-wall connectors preferably span substantially an entire length of the device. The inter-wall connectors may be integral with the internal tubular wall and the outer wall.

A viscosity of the cement is preferably set such that the cement can penetrate the area adjacent the bone fracture through the fenestrations in the outer wall.

In another exemplary embodiment, an intramedullary rod insertable into a cavity formed in a fractured bone is formed of a bioabsorbable synthetic material, wherein the intramedullary rod is cooperable with a biologically replaceable cement material to secure the intramedullary rod in the cavity.

In yet another exemplary embodiment, a method of treating a bone fracture using the described biologic intramedullary fixation device includes the steps of (a) forming a cavity in the bone that extends across the bone fracture; (b) inserting the biologic intramedullary fixation device in the cavity; and (c) injecting a biologically replaceable cement material into the annular space between the internal tubular wall and the outer wall. The method may further include, after step (c), inserting a set screw in an end of the internal tubular wall and covering the annular space or alternatively before step (c), inserting a set screw in an end of the internal tubular wall without covering the annular space.

Step (c) may be practiced by injecting the biologically replaceable cement material into the annular space until the biologically replaceable cement material penetrates the area adjacent the bone fracture through the fenestrations in the outer wall.

BRIEF DESCRIPTION OF THE DRAWINGS

These and other aspects and advantages will be described in detail with reference to the accompanying drawings, in which.

DETAILED DESCRIPTION OF THE INVENTION

With reference to FIGS. 1-4, the biologic intramedullary fracture fixation device 10 is shown in an exemplary application for proximal (subtrochanteric) femoral fracture repair.

As noted above, the fixation device described herein is suitable for fractures of all long bones. The device 10 includes an intramedullary rod 12 that is formed of a bioabsorbable synthetic material such as Polyglycolic acid or High Molecular Weight Polylactide polymers or a combination thereof. When combined with a cement material, the bioabsorbable synthetic material has a modulus of elasticity that is better than the native bone.

Figure 2:
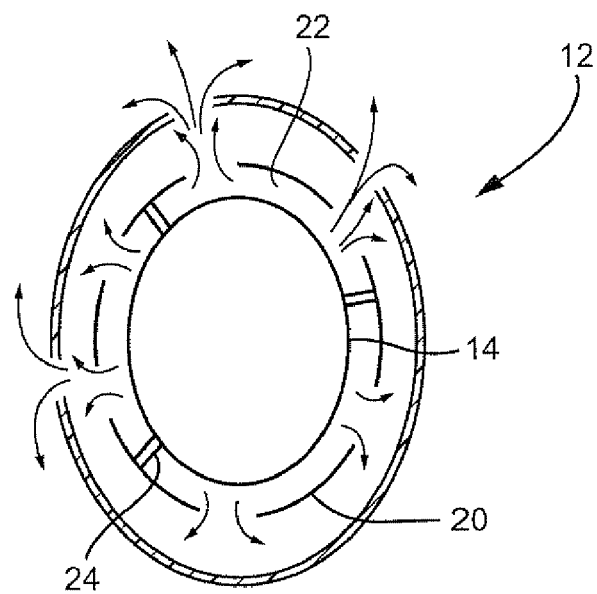
FIG. 2 is a cross sectional view through section II-II in FIG. 1.
Figure 3:
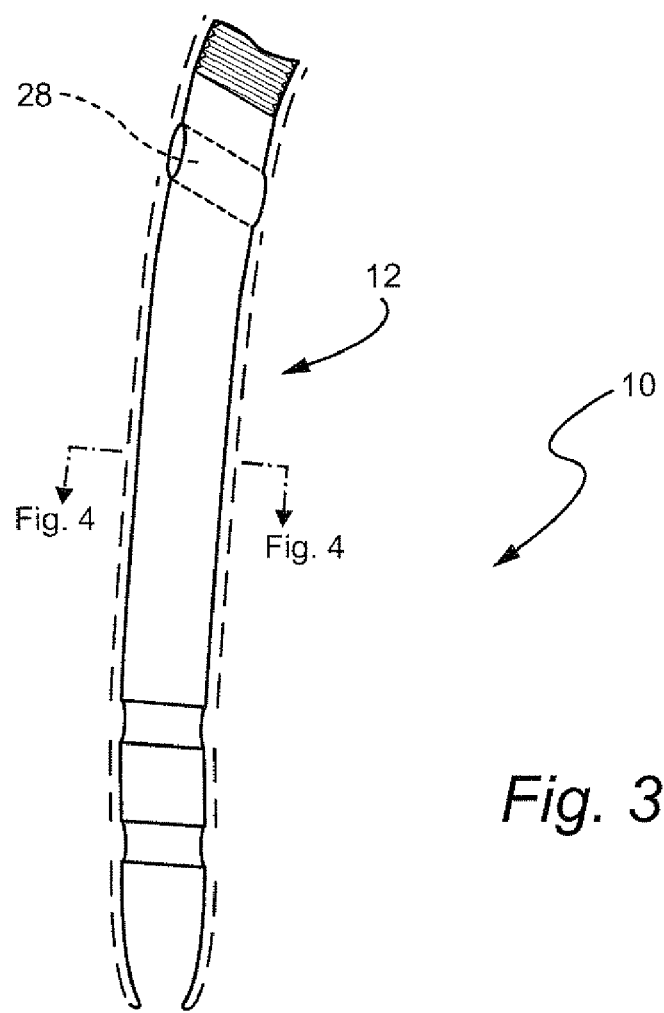
FIG. 3 shows the bioabsorbable intramedullary rod for femoral repair.
Figure 4:
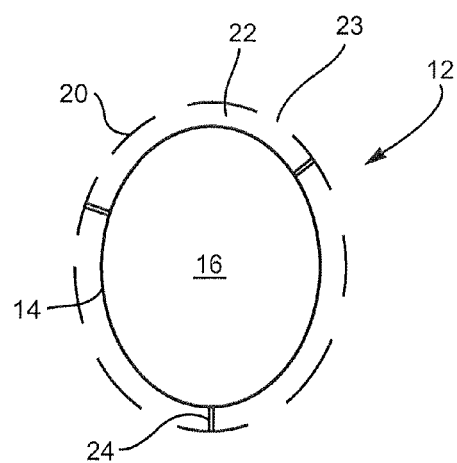
FIG. 4 is a cross sectional view through section IV-IV in FIG. 3.

As shown in FIGS. 2 and 4, the rod 12 includes an internal tubular wall 14 that defines an internal cavity 16. The internal tubular wall 14 may be provided with or without minimal fenestration at the site the fracture to permit extrusion of the cement centrally. A proximal end of the internal wall 14 is preferably sealed with a set screw 18 that stabilizes an interlocking nail N (in the exemplary case of the proximal femur) and also serves to prevent central injection of the cement. The internal wall 14 may be made smooth or ribbed to impart more rigidity. Preferably, a distal end of the internal wall 14 is left open to allow in-growth of vessels and resorption of the synthetic rod.

An outer wall 20 is coupled with and surrounds the internal tubular wall 14 with an annular space 22 therebetween. The outer wall is at least partially fenestrated 23 and is similarly formed of the bioabsorbable synthetic material. The outer wall 20 is preferably entirely fenestrated 23 except for its proximal and distal ends. Moreover, the fenestrations 23 are preferably more prominent in the region of the fracture to permit more cement extrusion at the fracture site to better augment the fixation.

A plurality of inter-wall connectors 24 connect the internal tubular wall 14 and the outer wall 20. The connectors 24 may run down the entire length of the rod 12 connecting the inner 14 and outer 20 walls, or may be designed to run short distances. The connectors 24 serve to maintain normal relations between the two walls 14, 20 and also impart further structural strength. In a preferred construction, the entire rod 12 is formed as an integral unit.

A biologically replaceable cement material is injectable into the annular space 22 between the internal tubular wall 14 and the outer wall 20. An exemplary material for the cement is hydroxyapatite. Preferably, a viscosity of the cement enables the cement to be injectable soon after mixing and allows penetration into the fracture site through the fenestrations 23 in the outer wall 20 of the rod 12. Preferably, the cement must set within a short period of time to permit some weight bearing within 24-48 hours. Over a period of time, the normal biological process of fracture healing should remove/remodel the cement to impart normal strength to the healing bone.

Figure 5:
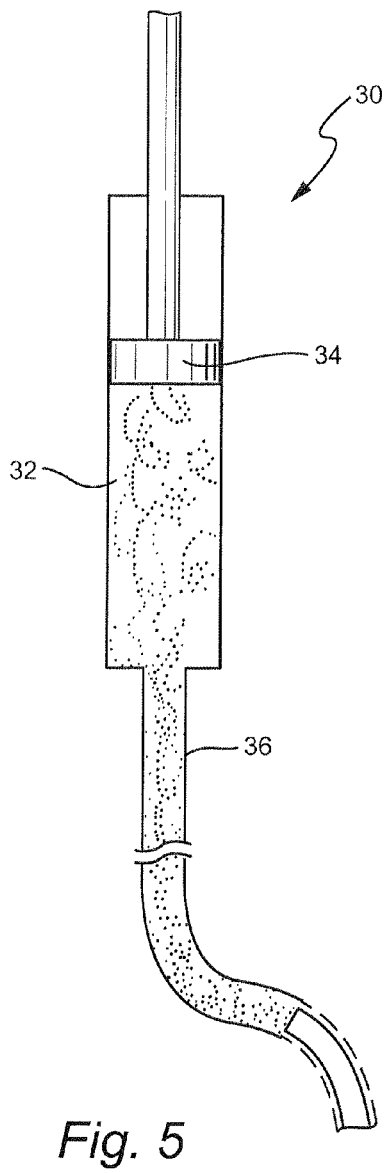
FIG. 5 shows a cement gun for injecting a cement material into the intramedullary rod.

In treating a bone fracture, a cavity 26 is formed in the bone and extends across the bone fracture. Such cavities are formed using a known reamer device or the like. The rod 12 is inserted into the cavity 26. In the exemplary application illustrated in FIG. 1, the rod 12 is provided with a tunnel 28 for receiving the interlocking nail N, which is used for treating a proximal (subtrochanteric) femoral fracture. With the rod 12 set in the cavity 26, the biologically replaceable cement is injected into the annular space 22 between the internal tubular wall 14 and the outer wall 20. With reference to FIG. 5, a cement gun 30 or the like may be used to inject the cement material. In a preferred construction, the cement gun 30 includes a cylinder 32 housing the cement material, and a plunger 34 that enables the cement material to be controllably injected into the rod 12 via a flexible tube 36.

Figure 1:
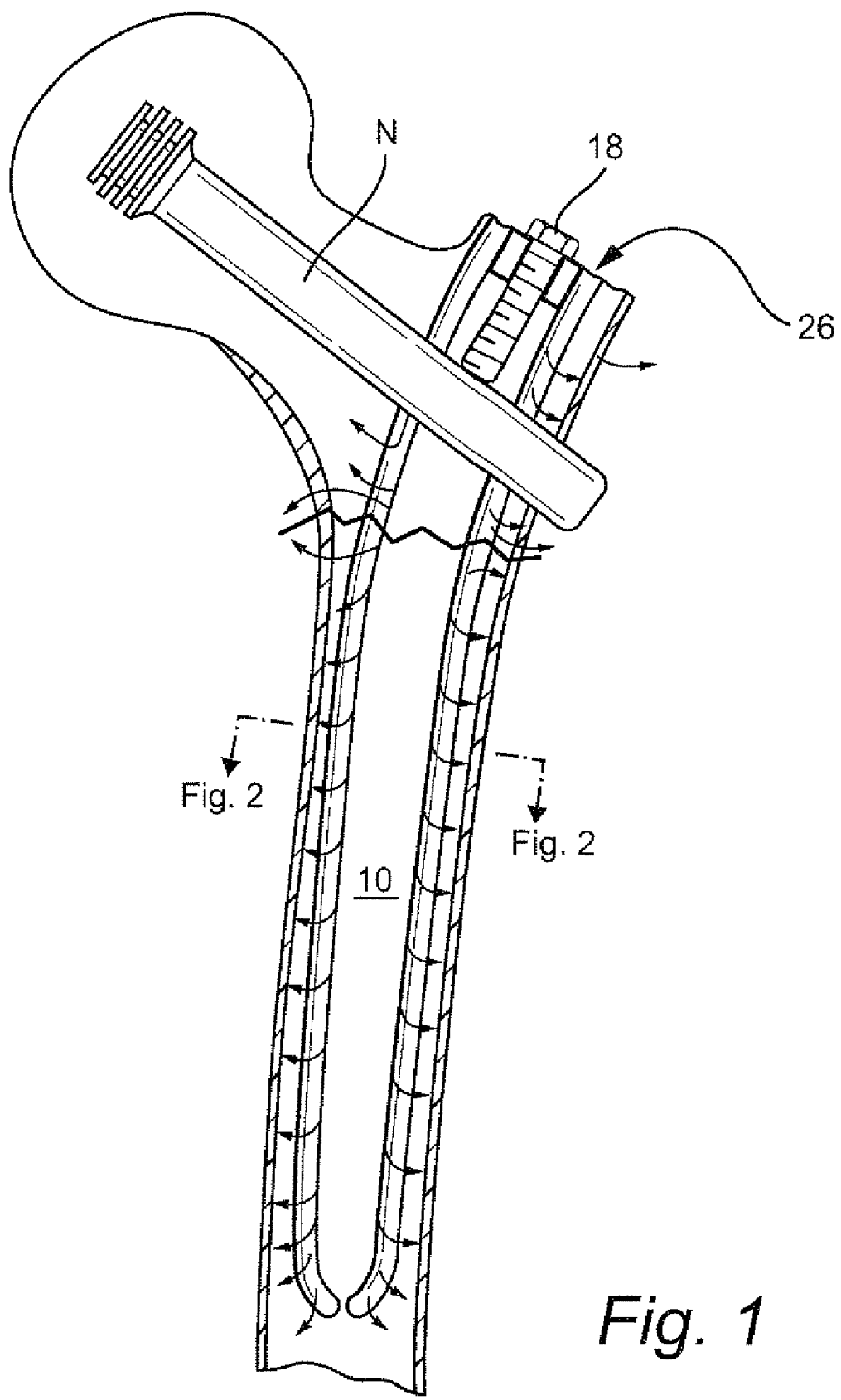
FIG. 1 is a sagittal view of the biologic intramedullary fixation device for proximal (subtrochanteric) femoral fracture repair.

In the exemplary embodiment illustrated in FIG. 1, the set screw 18 may be inserted in an end of the internal tubular wall 14 before or after cement injection. The set screw 18 if inserted prior to cement injection covers the opening of the internal tubular wall 14 and prevents central injection of the cement. Alternatively, the set screw 18 may be inserted after cement injection and may therefore cover the opening of the internal wall 14 and the annular space 22.

In the cement injection operation, the biologically replaceable cement material is injected into the annular space 22 until the material penetrates the area adjacent the bone fracture through the fenestrations 23 in the outer wall 20. As noted, the cement material preferably sets within a short period of time to permit some weight bearing within 24-48 hours, and over a period of time, the normal biological process of fracture healing should remove/remodel the cement to impart normal strength to the healing bone.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A method of treating a bone fracture using a biologic intramedullary fixation device including an internal tubular wall formed of a bioabsorbable synthetic material, and an outer wall coupled with and surrounding the internal tubular wall with an annular space therebetween, the outer wall being at least partially fenestrated and being formed of the bioabsorbable synthetic material, the method comprising:
   (a) forming a cavity in the bone that extends across the bone fracture;
   (b) inserting the biologic intramedullary fixation device in the cavity; and
   (c) inserting a set screw in an end of the internal tubular wall without covering the annular space; and
   (d) injecting a biologically replaceable cement material into the annular space between the internal tubular wall and the outer wall without injecting the biologically replaceable cement material within the internal tubular wall, wherein the biologically replaceable cement material penetrates the area adjacent the bone fracture through the fenestrations in the outer wall.

* * * * *